(12) United States Patent
Dalal

(10) Patent No.: US 11,869,644 B2
(45) Date of Patent: Jan. 9, 2024

(54) PROGRAMMED COMPUTER WITH SMART GOAL SETTING FOR DEPRESSION MANAGEMENT

(71) Applicant: Aashna Dalal, Porter Ranch, CA (US)

(72) Inventor: Aashna Dalal, Porter Ranch, CA (US)

( * ) Notice: Subject to any disclaimer, the term of this patent is extended or adjusted under 35 U.S.C. 154(b) by 664 days.

(21) Appl. No.: 16/573,748

(22) Filed: Sep. 17, 2019

(65) Prior Publication Data

US 2021/0082555 A1 Mar. 18, 2021

(51) Int. Cl.
*G16H 20/00* (2018.01)
*G16H 10/20* (2018.01)
*G16H 50/30* (2018.01)

(52) U.S. Cl.
CPC ............ *G16H 20/00* (2018.01); *G16H 10/20* (2018.01); *G16H 50/30* (2018.01)

(58) Field of Classification Search
CPC ........ G16H 20/00; G16H 10/20; G16H 50/30; G16H 20/10; G16H 20/70; G16H 40/63; G16H 50/70
See application file for complete search history.

(56) References Cited

U.S. PATENT DOCUMENTS

| | | | |
|---|---|---|---|
| 2009/0131758 A1* | 5/2009 | Heywood | A61B 5/0002 600/300 |
| 2013/0209977 A1* | 8/2013 | Lathan | G16H 50/20 434/236 |

* cited by examiner

*Primary Examiner* — Eliza A Lam

(74) *Attorney, Agent, or Firm* — Scott C Harris, Esq

(57) ABSTRACT

A depression scoring system obtains data from a large population of individuals including data about each of a plurality of different activities in relevant categories, and information about each of the individuals. Cohorts of individuals are defined as individuals who have similar statistical characteristics such as similar age, socioeconomic status, and sex. For each of the cohorts, a distribution of the data is obtained, and the scores of the top n %, e.g., 25% is set as a goal for the remaining members of the cohort. These goals are incrementally set and personalized for individual users to easily meet. This process is repeated constantly.

18 Claims, 3 Drawing Sheets

PROGRAMMED COMPUTER WITH SMART GOAL SETTING FOR DEPRESSION MANAGEMENT

BACKGROUND

Depression is a common mental disorder, especially among younger people. According to the Center for Disease Control and Prevention (CDC), as of 2016, suicide was the second leading cause of death for adolescents, ages 10-24. About 60 percent of people who commit suicide have had a mood disorder such as depression. This makes depression, and the treatment of depression, a national emergency.

Depression can also be associated with symptoms that can include feelings of hopelessness, loss of interest, fatigue, restlessness, shifts in appetite and weight, problems sleeping, and others.

Antidepressants can be used to attempt to combat both depression and its symptoms. However, many of the antidepressant drugs have their own host of side effects, and many people will simply refuse to take the antidepressants.

SUMMARY

An objective of the present invention is to use a programmed computer to carry out smart goal setting for depression management, by learning from a like "cohort," as defined herein, similar in demographics as defined by their statistical characteristics, to develop individualized goals for users. To do this, the system uses collected data on categories including sleep, diet, exercise, screen time, social interaction, medication compliance, and academic performance. The data can be continuously collected. By using continuously updated data, the system can frequently adjust and create appropriate goals for individuals that are based on their like cohort. Embodiments exploit computers that are programmed, as explained herein, to monitor and learn from performance in relevant categories of a like cohort and to determine goals for an individual based on the performance of others in their own cohort, which is not possible with other systems.

In an embodiment, the system defines a cohort for an individual based on that user's baseline demographics as measured by statistical characteristics including, but not limited to age, sex, race, family life and family size, comorbidities, and socioeconomic status. The computer learns from the cohort, and uses this learning capability to set smart goals for an individual within the cohort. For example, in one embodiment, the system may use the performance of the top 25% in a specific cohort to set goals for the remaining 75% of the users in that cohort.

BRIEF DESCRIPTION OF THE DRAWINGS

The different figures show different embodiments in which.

DETAILED DESCRIPTION

Figure 1:
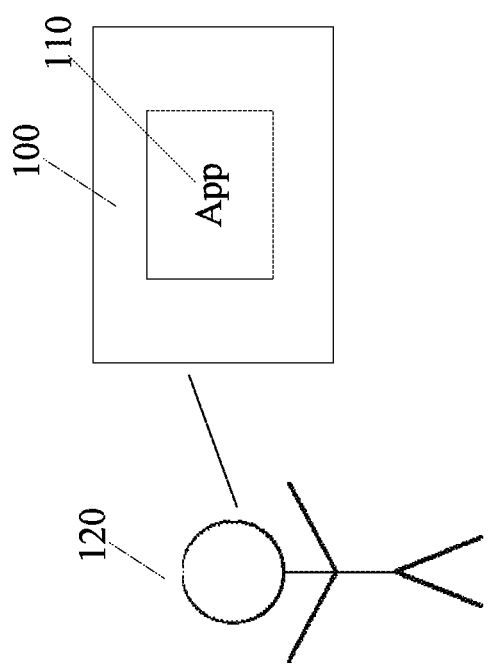
FIG. 1 shows the app running on a computer being used by a user.

In FIG. 1, a computer system 100, which is a local client, is shown running the application 110 under control of the user 120. The client 100 can be any kind of computer, including a desktop computer, phone, tablet, or any other computer. The computer communicates over a wired or wireless Internet connection.

Figure 2:
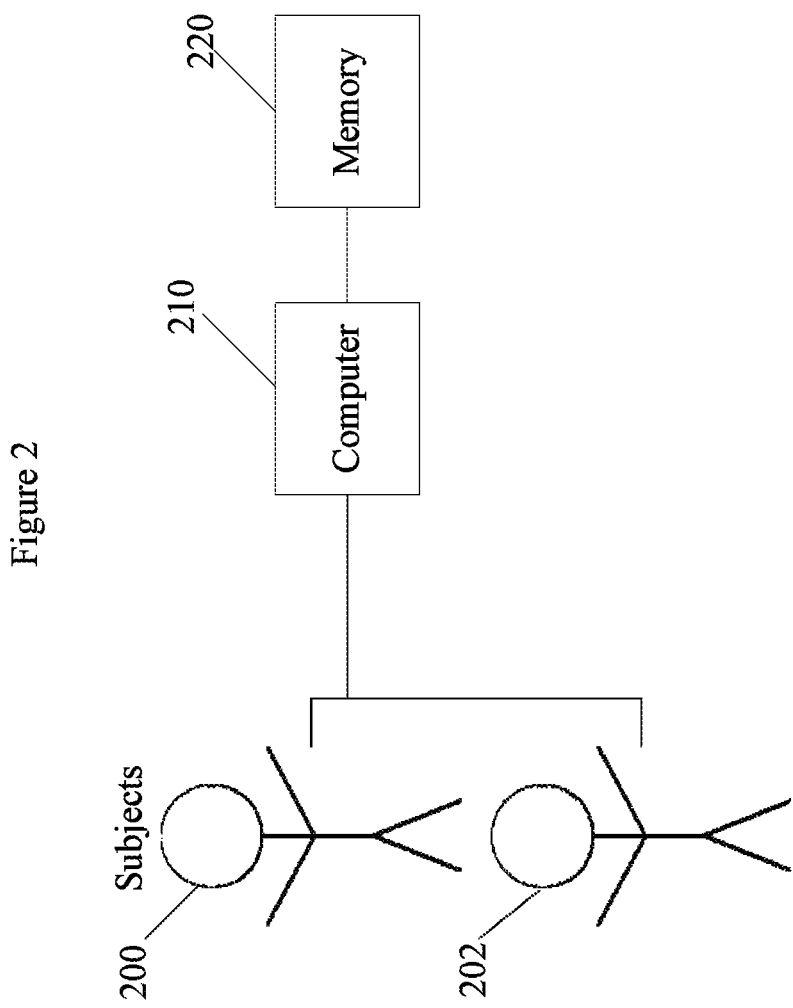
FIG. 2 shows a computer system that is used by multiple users for collection, storage, and processing of data.

An embodiment uses a computer to provide a depression scoring scale representing the amount of improvement needed for each of a plurality of people in a cohort and sets smart goals personalized for an individual user that are feasible to achieve based on the user's severity of depression and the user's capabilities to improve over a target time period. The system operates as described herein. FIG. 2 illustrates how each of a plurality of subjects 200, 202 provide their data to the computer system 210 which analyzes and stores the data in a memory system 220 as described herein. This data can be collected directly from user input, or from sensors on existing smart devices such as a smart phone, smart watch, smart bed, etc. An embodiment is explained with relative reference to the figures.

In an embodiment, all data is stored on a secure cloud for backup, restoration, population analytics, and to allow users to access the data on multiple platforms.

One embodiment compares data for people within a cohort and creates a numerical depression scoring system that displays the amount of improvement each user needs to achieve their target goal.

In this embodiment, each user is given a score between 0 and 4 for each category which translates to a total score that can range from 0 to 25. The score depends on actions, behaviors, and measurable performance of the user. One embodiment of the numerical scoring system is shown in table 1. A lower score represents a minimal detrimental impact of depression on one's daily life; whereas a higher score reflects a significant impact on one's ability to perform daily tasks as well as a danger to one's health.

TABLE 1

|   | Sleep | Diet | Screen Time | Exercise | Social Interaction | Medication Compliance | Academic Performance |
| --- | --- | --- | --- | --- | --- | --- | --- |
| 0 | 7.5-9 hours | Eats all 3 meals/eats appropriate number of calories | 1 hour or less | 1 hour daily | 3 times a week | Never misses a day | Maintains same grades over 2 years |
| 1 | 5.5-7.5 hours | Skips 1 meal/eats 250-500 more calories than recommended | 2.5 hours or less | 3 times a week | Once a week | Misses on weekends | Maintains same grades over 1 year |

TABLE 1-continued

| | Sleep | Diet | Screen Time | Exercise | Social Interaction | Medication Compliance | Academic Performance |
|---|---|---|---|---|---|---|---|
| 2 | 4-5.5 hours | Skips 2 meals/eats 500-750 calories more than recommended | 3 hours or less | 2 times a week | Once every two weeks | Misses one to two days a week | Fluctuation in grades from semester to semester |
| 3 | <4 hours | Skips 3 meals/eats over 750 calories more than recommended | 4 hours or less | Once a week | Once a month | Misses more than once a day | Sudden drop in grades over a semester |
| 4 | | | >4 hours | Rarely active | | Rarely remembers | Lack of effort and consistent drop in grades over a year |

Each user is scored, and assigned a baseline score based on the data that is initially collected.

The user is then given a target score (goal) based upon baseline scores of others in their cohort as described herein. The change in the score is monitored and tracked frequently, for example on a daily basis, to check for the user's improvement. The system tracks all users for changes in scores from their individual baseline scores using this continually updated data.

The system defines a number of different "cohorts" which are set as a group of users of similar statistical characteristics. For example, one cohort may be composed of users of age 16, male, and middle-class socio-economic background.

The system first starts by learning about the behaviors and current performance in relevant categories of the individuals in a cohort. There are various ways of obtaining data about the users. Three examples include direct user feedback, sensors, and visual feedback as explained herein.

Direct user feedback relies on user reported outcomes such as questionnaires, tests, and other things that are reported directly by users to the computer program.

It is believed that data that is obtained automatically may provide the ability to continuously update information about the user that inherently may be more accurate. One way to obtain data automatically is through sensors. This is collected using existing smart devices and applications which may be on the computer 100 or on other platforms. Examples of smart devices which can report their outputs to a computer system and can be used by this system include a smart phone, a smart bed, a smart scale, a fitness tracker, or a smart watch.

Another way that data is obtained is through visual feedback which uses cameras, facial recognition, and facial feature determination techniques to learn about and analyze the user's mood and level of depression. For example, visual feedback can provide data on a user's sleeping patterns. If the system consistently captures the user with baggy eyes and dark lines, the program can conclude that something is wrong with the user's sleeping habits and uses this information as a factor in determining the user's depression scores/need for improvement.

Figure 3:
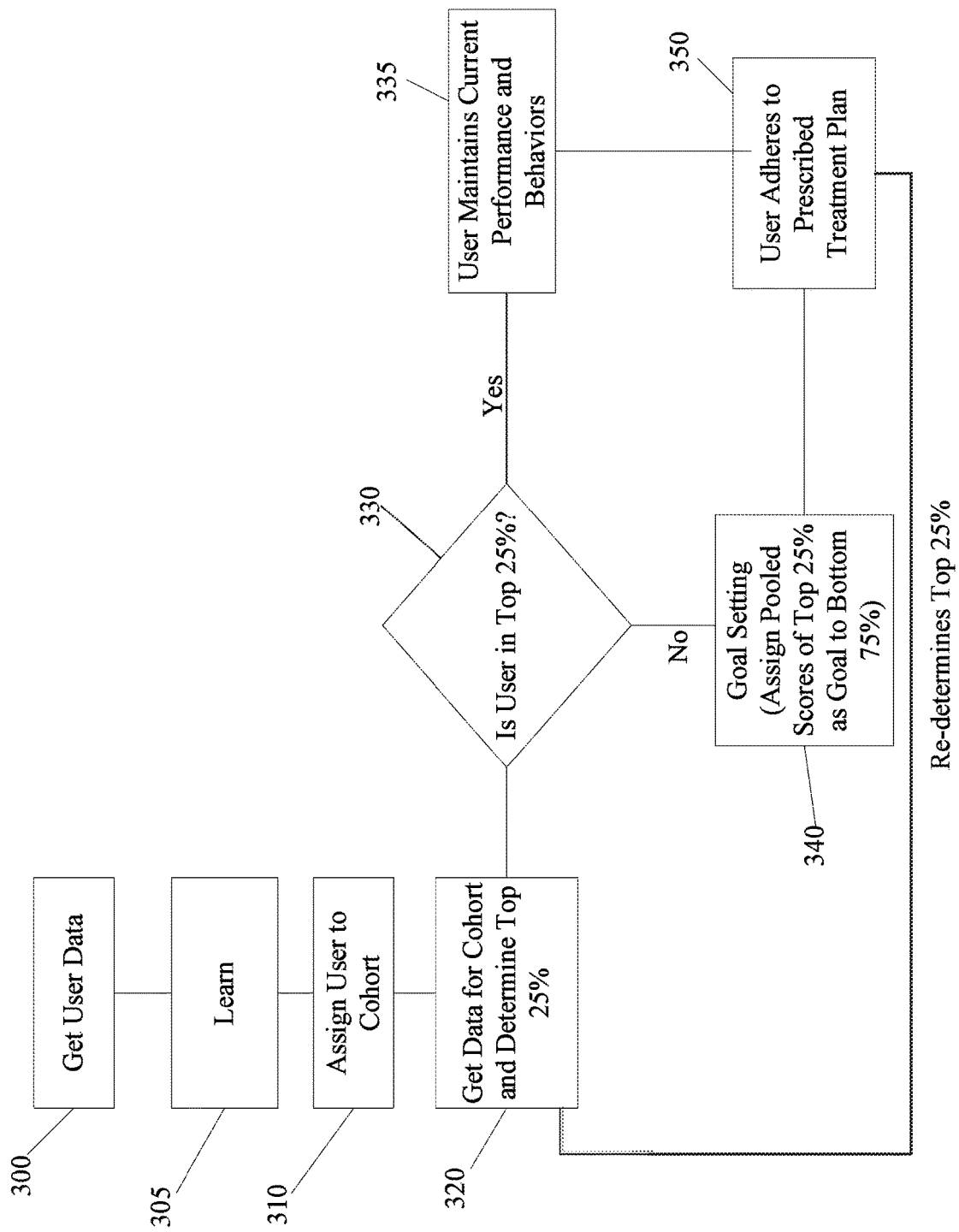
FIG. 3 shows an overall flowchart of operation of the system.

FIG. 3 illustrates a flowchart of operation of the system.

At 300, the system gets data from users prior to placing them in a cohort. The data includes information for the relevant categories described herein including sleep, diet, screen time, exercise, social interaction, medication compliance, and academic performance. Where possible, the system gets all available data about each individual from sensors and visual feedback, in addition to direct user feedback.

For example, when a user registers, they may automatically allow access to their smart phone to determine their amount of sleep, exercise, and screen time. The smart phone can automatically determine these things, and provide feedback to the system. The other categories, including diet, social interaction, medication compliance, and academic performance may normally be obtained through direct user feedback such as questionnaires. In selected cases, this data can also be obtained through methods such as smart pill bottle usage to obtain data on medication, or "friends in proximity" apps to obtain data on social interaction.

In this embodiment, all of the users' operations are scored from 0 to 4, based on specified criteria. Using this scale, the total score of an individual can range from 0-25. In the embodiment of table 1, the system looks at a number of categories such as sleep, diet, screen time, exercise, medication compliance, social interaction, and academic performance. In this embodiment, lower scores reflect a user's minimal need for improvement.

The system looks at sleep, and gives a score of 0 for sleep between 7½ and 9 hours. Similarly, the system gives a score of 1 for 5½ to 7½ hours of sleep, a score of 2 for 4 to 5½ hours of sleep, or a score of 3 for less than 4 hours of sleep.

The system also scores on diet, giving a lower score of 0 for eating all meals and eating the appropriate number of calories, and worse scores as meals are skipped or if the user overeats. The number of calories that is deemed appropriate is specific to the user's age, sex, and other factors as recommended by nationally determined dietary guidelines.

The system scores on screen time, giving the lowest score of zero for less than an hour of screen time.

The system scores on exercise, giving the lowest score of zero for an hour of daily exercise, and progressively worse scores for less exercise.

In a similar way, social interaction, medication compliance, and academic performance are also scored on a scale of 0 to 4 based on the user's behavior and performance as shown in table 1.

The table above displays a sample scoring system using these selected categories however, it should be understood that the scoring system itself can be adjusted as the data is continuously obtained. For example, it may be found that the amount of sleep or the scores for different amounts of sleep may need to be adjusted over time, which could be done herein. Also, the scoring scale is not limited to 0 to 4 as it can be made more granular depending on the availability of data. For example, the scale can be formatted on a range of 0 to 100. Finally, the scoring scale can also be adjusted to include other categories.

As shown in FIG. 3, 305 represents the system learning from the data it receives. The system needs to obtain and analyze enough data for the sample population before it can proceed to the next step.

Once a sufficient sample has been received, FIG. 3 shows that the system proceeds to the determination phase. At 310, each of a plurality of users is assigned to a "cohort". The cohort represents a group of users who are similar in a number of different ways. In an embodiment, each member of the cohort will have similar statistical characteristics such as the same sex, same age, and similar socioeconomic background. For example, if there are 1000 users, they may be divided into cohorts ranging in size of 20-100 users.

At 320, each user for each cohort is statistically analyzed, and the top n percentile of the cohort is determined based on their baseline scores in relevant categories, where n is a number that is either set in advance, or administrator-selectable. In one embodiment, n is 25, thus setting the top 25% of the cohort as the top scores. At 330, the system separates users based on whether or not they fall into the top 25% of their cohort. If the user is within the top 25% of their cohort, they will continue to maintain their current performance and behaviors at 335 and adhere to their prescribed treatment plan at 350. FIG. 3 shows that all users are reassessed as the system returns to 320 and re-determines the top 25% of the cohort using continually updated data.

At 340, the scores of the top 25% of people within a cohort is pooled to form a pooled score, and that pooled score is assigned as a goal to every user who is in the bottom 75% of the cohort. These goals will be adjusted and personalized based on how much the user needs to improve and the user's capability to improve. For example, if a user's baseline score falls significantly out of range of the pooled scores of users in the top 25% of their cohort, they will be assigned incremental goals that are feasible and personalized for them. The system creates these smart goals by continuing to learn about the users and tracking changes in their scores on a daily basis to understand how much the users are able to improve over certain periods of time.

At this point, each user within a cohort can be analyzed, to determine the amount of improvement they need to reach their target score. In addition, each user is given specific goals. For example, if users in the top 25% of a cohort have a sleep time between 5½ and 7½ hours, then this is provided as a goal to each user in the bottom 75% of the cohort. The embodiment describes a hypothetical "user 1"; however, every user will have personalized goals at any point in time as assigned at 340 based on scores in their cohorts. The path and time period to achieve these scores will vary from individual to individual.

Examples of the cohorts and the goal setting is provided herein.

Sample Cohort:
Age: 15
Sex: Male
Race: Caucasian
Economic Status: Middle-Class
Household Income: $75,000 (more generally between $60 k-100K)
Family Life: Parents are together
Comorbidities: none Everyone with these characteristics becomes part of this cohort.

The system gets data for these cohorts at 320, and finds the pooled scores of the top 25%, which in one embodiment is as follows.

Top 25% Score:

|  | Category | | | | | | |
|---|---|---|---|---|---|---|---|
| Sleep | Diet | Screen Time | Exercise | Social Interaction | Medication Compliance | Academic Performance | Total |
| Score 2 | 0 | 2 | 1 | 2 | 0 | 0 | 7 |

Goal Setting:

This cohort includes users who were of age 15, male, living with both parents, Caucasian, and middle-class with an approximate household income of $75,000. Within this cohort, the pooled score of the top 25% was 7 as shown in the table. As a result, the following legend/categories are created for this cohort. The categories represent the amount of improvement one needs to reach their target score:

0-7=healthy
8-12=needs mild improvement
12-17=needs moderate improvement
>17=needs significant improvement Consequently, in this example, the goal of the remaining 75% of users in the cohort is to bring their score down to 7 or less. This can be done a number of ways as scores can be improved drastically in some categories while very minutely in others with the same final score results. However, the optimum way for a user to improve their score can be recommended by a medical professional or through the use of other smart applications that can prescribe a personalized treatment plan. Additionally, it may be obvious if a user needs to focus on one category over another based on how drastically their score falls outside of the desired range. On the other hand, the goal for those who are already within the top 25% of their cohort is to maintain their current routine and habits. At 350, the user makes changes in their lifestyle and adheres to a prescribed treatment plan. At this point, FIG. 3 shows that the system returns to 320 to obtain data for the cohort and adjust the definition of the top 25% within a cohort based on the changes in users' scores.

Note that other cohorts will have different goals set, based on the values set forth by the population.

To understand how goals are set for users within this cohort, a sample subject is explained below.

Sample Subject: John Smith
Age: 15
Sex: Male
Race: Caucasian
Economic Status: Middle-Class
Household Income: $75,000
Family Life: Parents are together
Comorbidities: none Initial Score relative to "target" set by those who fall in the 75$^{th}$ percentile or greater:

| | Category | | | | | | |
|---|---|---|---|---|---|---|---|
| | Sleep | Diet | Screen Time | Exercise | Social Interaction | Medication Compliance | Academic Performance | Total |
| Score of Sample User | 3 | 2 | 4 | 2 | 3 | 2 | 2 | 18 |
| Target Score | 2 | 0 | 2 | 1 | 2 | 0 | 0 | 7 |

Summary of Finding:

This subject clearly falls into the cohort described above based on his demographics. However, the score for this sample subject, John Smith, is much higher than that of the top 25% within his cohort population. According to the scoring factors given above, this subject has a score of 18, and hence needs significant improvement to reach his target score. Therefore, John Smith's goal would essentially be to improve his score until he reaches the benchmark set by the top quarter of the population in his cohort. However, his initial goal may simply be to improve his score to shift his status from needing significant improvement to needing moderate improvement. By creating smaller, incremental goals, the user can more easily achieve their final goal. These incremental goals are constantly adjusted based on the user's ability to improve over a targeted time period. The goals, themselves, can be further broken down into categories.

Sleep (3):

For example, if John's initial score in the sleep category is three, he is currently sleeping for approximately less than 4 hours on a daily basis. His initial personalized goal, however, may be to bring his score down to 2 by getting at least 4 to 5.5 hours of sleep on a daily basis. He can use various sleep management techniques such as alarms, smart lighting, smart bed features, and music to help him achieve this goal. In order to do that, the system may assume, for example, that John always wakes up at the same time every morning, since presumably John is a high school student. Assuming John wakes up at 6:00 every morning, and his goal is to obtain approximately 5.5 hours of sleep, he needs to be asleep by 12:30 AM. These changes in John's sleep routine can be recommended by a medical professional, a medical expert system, or through the use of other smart applications that may prescribe a personalized treatment plan.

Once John reaches his goal, he may be encouraged to further improve his score. To achieve this, a medical professional may recommend a consistent sleep routine for John to adhere to.

Diet (2):

John's current score in the diet category is a 2, meaning that he consistently skips two meals a day. A score of 2 could also suggest that John is eating 500 to 750 more calories than his recommended intake. However, in this case, it can be assumed that a score of 2 means that he is skipping two meals a day. His eventual goal is to bring this score down to zero by making sure to eat all three meals on a daily basis/eat an appropriate amount of calories. He could be encouraged to do this through diet management techniques such as an alarm or reminder system or a calorie tracker to ensure that he is getting enough nutrition on a daily basis.

Determining what meals John is skipping may help the system link two categories to each other, allowing John to improve faster. For example, if the system determines that John is consistently skipping breakfast, it might be related to the fact that John is consistently waking up late. Therefore, scores in both the sleep and diet categories can be improved simultaneously if John successfully adjusts his sleep schedule.

Screen Time (4):

Based upon metadata collected initially, the system determined that John uses electronics excessively for over 4 hours a day as his current score in this category is a 4. His goal is to bring his score down to 2 with a total screen usage of less than 3 hours a day. To do this, John can use features on a smart phone or other smart devices that block applications after a certain period of time or during a certain time of day to ensure that he cannot even gain access to additional screen time.

Exercise (2):

John engages in moderate physical activity, as the system determined that he engages in physical activity approximately 2 times a week. His goal, however, is to bring his score down to 1 by being physically active at least three times a week. Therefore, significant improvement is not necessary in this category. John may be able to use his improved exercise routine as a motivator to improve scores in other categories as described herein.

Social Interaction (3):

The system determined that John is not very socially involved as he only engages in social events about once a month. His goal is to bring this score down to a 2, forcing him to be socially engaged at least once every two weeks. Using this information, a clinician or other smart applications may be able to recommend options such as participation in community service projects as a way to improve John's score in the category of social interaction. Additionally, to improve John's performance in multiple categories such as exercise and social interaction, he might be encouraged to join a local sports team or go to the gym and attend classes so he can improve his exercise routine while also being socially engaged.

Medication Compliance (2):

With a current score of 2, John is missing his medication about one to two days a week. His goal is to bring this score down to zero. To achieve this goal, John can use techniques such as smart pill bottle usage or a simple alarm/reminder system.

Academic Performance (2):

With a current score of two, John's grades tend to fluctuate from semester to semester. His goal is to bring this score down to zero and be able to maintain his grades overtime. By improving scores in other categories, John may automatically also improve his score in this category. For example, if he successfully improves his score in the category of screen time, he may have fewer distractions allowing him to increase his focus on academics. Scores in all of these categories can also be improved through the use of other smart applications that provide personalized treatment plans.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system of setting goals for depression in a user and carrying out depression reducing operations, comprising:
    a computer system, running a computer application,
    the computer system initially receiving a plurality of user data from a universe of different people, and analyzing the user data to learn information about the users,
    the computer system assigning each user to a cohort, where the cohort includes a plurality of users, all of the users in a cohort having all of
    a similar age,
    a same sex,
    a similar socioeconomic background, and
    a same family situation, where the family situation is one of living with parents who are together, or living with parents who are not together;
    and where the cohort is a subset of the universe;
    for each cohort, the computer system analyzing all the users in the cohort, to determine a score for each of a plurality of categories of activities associated with depression, where the categories of activities associated with depression include at least sleep, diet, screen time value as a number of hours per unit time that a user uses their electronic device, exercise, and academic performance, and where the score includes individual scores for each of the plurality of categories associated with depression;
    defining within the cohort, a top value of scores, and pooling the top value of scores to set a target score; and
    setting the pooled scores as a goal for each user in the bottom n percent of the cohort, wherein the computer determines the user using the electronic device for a certain amount of time per unit period of time, and where the electronic device automatically blocks applications from running based on the computer determining the user using the using the electronic device for a certain amount of time per unit period of time.

2. The system as in claim 1, wherein the computer system also analyzes other categories including social interaction and medication compliance.

3. The system as in claim 1, wherein the computer system analyzes hours of sleep as the sleep value, numbers of meals missed/calorie intake as the diet value, number of hours on an electronic device as the screen time value, number of times per week exercising as the exercise value, and consistency of grades over specified periods of time as the academic performance value.

4. The system as in claim 1, wherein the computer system receives user data by obtaining manually-completed questionnaires from users.

5. The system as in claim 4, wherein the computer system also receives data from a user's smart phone and other smart devices which automatically monitor parameters of the user's activities.

6. The system as in claim 1, wherein the top value of scores is a 25% top value of scores.

7. The system as in claim 1, wherein the computer automatically determines that the user has a low score in a first category that is effected by a low score in a second category, and causing the user to adjust the second category in order to change the score in the first category.

8. The system as in claim 1, wherein the computer automatically determines that the user is skipping breakfast meal, and also waking up late, and requests adjustment of the user's sleep schedule to adjust both the user skipping the breakfast meal and not getting enough sleep.

9. The system as in claim 8, wherein the additional user data is obtained daily.

10. A method of setting goals for actions in a user and carrying out depression reducing operations, comprising:
    in a computer running a computer application, the computer method initially receiving a plurality of user data from a universe of different people, and analyzing the user data to learn information about the user data,
    the computer assigning each user to a cohort, where the cohort includes a plurality of users all of the users in a cohort having all of
    a similar age,
    a same sex,
    a similar socioeconomic background, and
    same family situation, where the family situation is one of living with parents who are together, or living with parents who are not together;
    and where the cohort is a subset of the universe;
    for each cohort, analyzing all the users in the cohort, to determine a score for each of a plurality of categories of activities associated with depression, where the categories of activities associated with depression include at least sleep, diet, screen time value as a number of hours per unit time that a user uses their electronic device, exercise, and academic performance, and where the score includes individual scores for each of the plurality of categories associated with depression;
    defining within the cohort, a top value of scores, and pooling the top value of scores to set a pooled score set representing a target score;
    setting the pooled score set as a goal for each user in the cohort; and
    determining the user using the electronic device for a certain period of time relative to the goal, and automatically blocking applications from running on the computer beyond the certain period of time.

11. The method as in claim 10, wherein the computer also analyzes other categories including social interaction and medication compliance.

12. The method as in claim 10, wherein the computer analyzes hours of sleep, as the sleep value, numbers of meals missed/calorie intake as the diet value, number of hours on an electronic device as the screen time value, number of times per week exercising as the exercise value, and consistency of grades over specified periods of time as the academic performance value.

13. The method as in claim 10, wherein the computer receives user data by obtaining manually-completed questionnaires from users.

14. The method as in claim 13, wherein the computer also receives data from a user's smart phone and other smart devices which automatically monitor parameters of the user's activities.

15. The method as in claim 10, wherein the top value of scores is a 25% top value of scores.

16. The method as in claim 10, further comprising automatically determining that the user has a low score in a first category that is effected by a low score in a second category, and causing the user to adjust the second category in order to change the score in the first category.

17. The method as in claim 10, further comprising automatically determining that the user is skipping breakfast meal, and also waking up late, and requests adjustment of the user's sleep schedule to adjust both the user skipping the breakfast meal and not getting enough sleep.

18. The method as in claim 17, wherein the additional user data is obtained daily.

* * * * *